United States Patent
Tripathi et al.

(10) Patent No.: US 10,817,994 B2
(45) Date of Patent: Oct. 27, 2020

(54) METHOD AND SYSTEM FOR OBTAINING A TRUE SHAPE OF OBJECTS IN A MEDICAL IMAGE

(71) Applicant: Siemens Healthcare GmbH, Erlangen (DE)

(72) Inventors: Gaurav Tripathi, Lucknow (IN); Mayur Betharia, Bangalore (IN)

(73) Assignee: Siemens Healthcare GmbH, Erlangen (DE)

( * ) Notice: Subject to any disclaimer, the term of this patent is extended or adjusted under 35 U.S.C. 154(b) by 203 days.

(21) Appl. No.: 16/110,723

(22) Filed: Aug. 23, 2018

(65) Prior Publication Data

US 2019/0087947 A1 Mar. 21, 2019

(30) Foreign Application Priority Data

Sep. 18, 2017 (EP) .................................. 17191582

(51) Int. Cl.
*G06T 5/00* (2006.01)
*A61B 6/00* (2006.01)
*G06T 7/62* (2017.01)

(52) U.S. Cl.
CPC .............. *G06T 5/006* (2013.01); *A61B 6/585* (2013.01); *G06T 7/62* (2017.01); *G06T 2207/10112* (2013.01); *G06T 2207/10116* (2013.01)

(58) Field of Classification Search
CPC . G06T 2207/10112; G06T 2207/10116; G06T 5/006
See application file for complete search history.

(56) References Cited

U.S. PATENT DOCUMENTS

| 5,771,308 | A  | * | 6/1998  | Florent   | G06T 7/0012 |
|           |    |   |         |           | 382/130     |
| 6,289,235 | B1 | * | 9/2001  | Webber    | A61B 6/12   |
|           |    |   |         |           | 378/23      |
| 9,256,939 | B1 | * | 2/2016  | Bediz     | A61B 6/502  |
| 2004/0086082 | A1 | * | 5/2004 | Foos      | A61B 5/1072 |
|           |    |   |         |           | 378/163     |
| 2004/0264758 | A1 | * | 12/2004 | Christoph | G01B 11/005 |
|           |    |   |         |           | 382/141     |

(Continued)

OTHER PUBLICATIONS

Dobbins III, James T., and Devon J. Godfrey. "Digital x-ray tomosynthesis: current state of the art and clinical potential." Physics in medicine & biology 48.19 (2003): p. R65-R106.

(Continued)

*Primary Examiner* — Gandhi Thirugnanam
(74) *Attorney, Agent, or Firm* — Lempia Summerfield Katz LLC (57) ABSTRACT

A method and system are provided for obtaining a true shape of objects in a medical image. The method includes receiving X-ray stand geometry parameter values, an $Angle_{point}$ and an $Angle_{stand}$ values; selecting a plurality of pixels representing an object in the X-ray image; and determining magnification of each pixel in the X-ray image, that enables accurate determination of size and shape of imaged objects. The method may include determining an actual size of the object in the X-ray image and selectively reshaping the object in the X-ray image to obtain a true shape of the object.

16 Claims, 5 Drawing Sheets

(56) References Cited

U.S. PATENT DOCUMENTS

| | | | |
|---|---|---|---|
| 2008/0031506 A1* | 2/2008 | Agatheeswaran | G06T 7/0012 |
| | | | 382/132 |
| 2008/0063304 A1* | 3/2008 | Russak | A61B 6/583 |
| | | | 382/298 |
| 2013/0215114 A1* | 8/2013 | Cherkashin | A61B 6/584 |
| | | | 345/420 |
| 2014/0219500 A1* | 8/2014 | Moehrle | G16H 30/20 |
| | | | 382/103 |
| 2014/0294138 A1* | 10/2014 | Jerebko | G06T 11/003 |
| | | | 378/4 |
| 2016/0042571 A1* | 2/2016 | Mikheev | G06T 7/85 |
| | | | 345/419 |
| 2018/0098820 A1* | 4/2018 | Park | A61B 6/12 |
| 2018/0188192 A1* | 7/2018 | Artemiev | G01N 23/201 |
| 2019/0087947 A1* | 3/2019 | Tripathi | G06T 7/62 |

OTHER PUBLICATIONS

European Office Action for European Patent Application No. 17191582.0-1906 dated Dec. 20, 2017.

Kolitsi, Z., et al. "A multiple projection method for digital tomosynthesis." Medical physics 19.4 (1992): p. 1045-1050.

National Electrical Manufacturers Association: "DICOM Standard, part PS3.3"; (chapter C.8.19.6.9; X-Ray Projection Pixel Calibration Macro); XP055433169; 2004. p. 558-562.

* cited by examiner

| Measurement # | Value | Error % |
|---|---|---|
| X1 | 31.05 | 2.66 |
| X2 | 27.29 | 14.45 |
| X3 | 24.35 | 23.67 |

FIG 5

METHOD AND SYSTEM FOR OBTAINING A TRUE SHAPE OF OBJECTS IN A MEDICAL IMAGE

The application claims the benefit of European Patent Application No. EP 17191582.0, filed Sep. 18, 2017, which is hereby incorporated by reference in its entirety.

FIELD OF TECHNOLOGY

The present disclosure relates to a method and hardware and a software system of obtaining a true shape of an object in a medical image. The method includes selecting a plurality of pixels representing an object in the medical image and determining magnification of each pixel of the object in the medical image.

BACKGROUND

Pixel spacing represents the physical distance between two adjacent pixels. In order to measure an object in a medical image, such as an X-ray image, the pixel spacing has to be accurately determined. Image calibration techniques well known in the prior art determine the pixel spacing by assuming the patient to be positioned in the two-dimensional plane perpendicular to the central axis of the X-ray beam. Determination of pixel spacing in an X-ray image may be performed by several techniques that may be well known to a person skilled in the art. For example, a geometric calibration may be performed where magnification is determined based on the position of X-ray tube, X-ray detector, object being examined, and image iso-center. This approach determines the geometric beam path from X-ray source to X-ray detector and calculates the magnification of the object interfering with the beam. In an alternative method, pixel spacing is determined by dividing a known length of the object with the pixels representing the object. The abovementioned calibration techniques assume the object magnification within the X-ray image to be uniform. However, if the object plane is not perpendicular to the axis of the X-ray beam, the magnification across the X-ray image may not be uniform. Therefore, due to variable magnification across the image, the measurements obtained of the object in the X-ray image are inaccurate. Furthermore, variable magnification may also render the objects in the X-ray image to be deformed. This may also cause error in registering the X-ray image with other modality in hybrid procedures.

SUMMARY AND DESCRIPTION

The scope of the present disclosure is defined solely by the appended claims and is not affected to any degree by the statements within this description. The present embodiments may obviate one or more of the drawbacks or limitations in the related art.

The object of the disclosure is to correct the magnification across a medical image so as to accurately determine the size and shape of the imaged objects.

Based on the aforementioned methods, an actual size of the object in the medical image is determined and the object in the medical image is selectively reshaped to obtain a true shape of the object.

A method of obtaining a true shape of an object in a medical image is provided herein. The method includes receiving X-ray stand geometry parameter values, an $Angle_{point}$, and an $Angle_{stand}$ values. The X-ray stand geometry parameter values, an $Angle_{point}$, and an $Angle_{stand}$ values may be received, for example, from an imaging unit during acquisition of medical image. Alternatively, if the medical image is an image which is obtained from a database, the stand parameters and angle values may be obtained from Digital Imaging and Communications in Medicine (DICOM) data.

According to an embodiment, the method further includes selecting a plurality of pixels representing an object in the medical image. The medical image may be, but not limited to, for example, an X-ray image. The X-ray image may be a conventional radiographic image or a live fluoroscopic X-ray image.

According to an embodiment, the method further includes determining magnification of each pixel in the X-ray image using the X-ray stand geometry parameter values, an $Angle_{point}$, and an $Angle_{stand}$ values. Magnification of a pixel is influenced by an angle made by a line joining a point on the X-ray image to X-ray source and a line joining a center of the X-ray image to the X-ray source.

According to another embodiment, the method further includes selectively reshaping the object in the X-ray image. The selective reshaping may be performed using the determined magnification of each pixel. The selective reshaping of the object enables obtaining a true shape of the object.

According to an embodiment, in selecting a plurality of pixels representing the object on the medical image, a plurality of pixels representing the object is identified and from the plurality of identified pixels, a sequence of connecting pixels which represent a contour of the object is selected. The plurality of pixels may be chosen by a user by drawing a contour on the medical image by dragging a cursor around the desired object. On drawing the contour, a plurality of pixels in the desired area on the object is selected. Alternatively, the plurality of pixels representing the object may be identified automatically by use of one or more landmarks for object identification. The contour of the object may therefore be selected automatically based on, for example, shape based models or appearance based models for object segmentation. Selection of a plurality of pixels in the X-ray image enables identification a region of interest in the X-ray image.

According to another embodiment, the method further includes determining an actual size of the object on the medical image. The actual size of the object is determined by calculating pixel spacing for each pixel representing the contour. Pixel spacing is a physical distance between the centers of two two-dimensional pixels. Calculating pixel spacing for each pixel along the contour of the object enables determination of actual size of the object accurately. According to the state of the art, the size of an object in an X-ray image is determined using fixed pixel spacing between two pixels. The determined pixel spacing value between two adjacent pixels is assumed to be uniform across the X-ray image. However, if magnification factor across the pixels is different, use of fixed pixel spacing to determine actual size of the object may provide erroneous results. Therefore, calculating pixel spacing values for each pixel along the contour of the object enables determination of actual size of the object irrespective of change in magnification of pixels.

According to yet another embodiment, the reshaping of the object in the medical image is achieved by selecting a plurality of pixels representing a region of interest on the X-ray image. The region of interest may be, for example, an object in the X-ray image. The plurality of pixels may be selected, for example, manually during post processing of the X-ray image. Alternatively, the plurality of pixels may also be chosen automatically by inputting stand position, beam ISO center, and table-object distance. A reference pixel from the plurality of pixels is selected and magnification of the plurality of pixels present around the reference pixel is adjusted according to the magnification of the reference pixel. Therefore, pixels around the reference pixels are shrunk or stretched depending upon the difference in the magnification between the reference pixel and the neighboring plurality of pixels. Thus, a sequence of uniformly magnified pixels is generated representing the actual shape of the object. The true shape of the object may be displayed on an output unit, (for example, a display unit). Advantageously, the disclosure achieves determination of true shape of an object in a medical image during real-time acquisition of the medical image. For example, in a real-time fluoroscopic imaging, the true shape of the object being imaged may be determined during the interventional procedure. The obtained true shape of the object may be displayed on the display unit for further analysis by a physician. Therefore, the physician receives accurate imaging information, thereby avoiding the delay in post processing of the medical image.

According to an embodiment, the medical image is an X-ray image.

The object of the disclosure is also achieved by a system for obtaining a true shape of an object in a medical image. According to an embodiment, the system includes a processing unit and an image database coupled to the processing unit. The image database includes one or more medical images that may have been acquired from a medical imaging unit or, for example, obtained from an external source. The system further includes a memory coupled to the processing unit. The memory includes a magnification correction module. The magnification correction module is configured to receive X-ray stand geometry parameter values, an $Angle_{point}$, and an $Angle_{stand}$ values. The X-ray stand geometry parameter values, an $Angle_{point}$, and an $Angle_{stand}$ values may be received, for example, from an imaging unit during acquisition of medical image. Alternatively, if the medical image is an image which is obtained from a database, the stand parameters and angle values may be obtained from DICOM data.

According to an embodiment, the magnification correction module is further configured to select a plurality of pixels representing an object in the medical image. The medical image may be, but not limited to, for example, an X-ray image. The X-ray image may be a conventional radiographic image or a live fluoroscopic X-ray image.

According to another embodiment, the magnification correction module is further configured to determine magnification of each pixel in the X-ray image using the X-ray stand geometry parameter values, an $Angle_{point}$, and an $Angle_{stand}$ values. Magnification of a pixel is influenced by an angle made by a line joining a point on the X-ray image to X-ray source and a line joining a center of the X-ray image to the X-ray source.

According to an embodiment, the magnification correction module is further configured to selectively reshape the object in the X-ray image to obtain a true shape of the object. The selective reshaping may be performed using the determined magnification of each pixel. The selective reshaping of the object enables obtaining a true shape of the object.

According to an embodiment, in selecting a plurality of pixels representing the object on the medical image, the magnification correction module is configured to identify a plurality of pixels representing the object and select, from the plurality of identified pixels, a sequence of connecting pixels which represent a contour of the object. The plurality of pixels may be chosen by a user by drawing a contour on the medical image by dragging a cursor around the desired object. On drawing the contour, a plurality of pixels in the desired area on the object is selected. Alternatively, the plurality of pixels representing the object may be identified automatically by use of one or more landmarks for object identification. The contour of the object may therefore be selected automatically based on, for example, shape based models or appearance based models for object segmentation. Selection of a plurality of pixels in the X-ray image enables identification a region of interest in the X-ray image.

According to another embodiment, the magnification correction module is further configured to determine an actual size of the object on the medical image. The actual size of the object is determined by calculating pixel spacing for each pixel representing the contour. Pixel spacing is a physical distance between the centers of two two-dimensional pixels. Calculating pixel spacing for each pixel along the contour of the object enables determination of actual size of the object accurately. According to the state of the art, size of an object in an X-ray image is determined using fixed pixel spacing between two pixels. The determined pixel spacing value between two adjacent pixels is assumed to be uniform across the X-ray image. However, if magnification factor across the pixels is different, use of fixed pixel spacing to determine actual size of the object may provide erroneous results. Therefore, calculating pixel spacing values for each pixel along the contour of the object enables determination of actual size of the object irrespective of change in magnification of pixels.

According to yet another embodiment, the in selectively reshaping the object in the medical image, the magnification correction module is configured to select a plurality of pixels representing a region of interest on the X-ray image. The region of interest may be, for example, an object in the X-ray image. The plurality of pixels may be selected, for example, manually during post processing of the X-ray image. Alternatively, the plurality of pixels may also be chosen automatically by inputting stand position, beam ISO center, and table-object distance. A reference pixel from the plurality of pixels is selected and magnification of the plurality of pixels present around the reference pixel is adjusted according to the magnification of the reference pixel. Therefore, pixels around the reference pixels are shrunk or stretched depending upon the difference in the magnification between the reference pixel and the neighboring plurality of pixels. Thus, a sequence of uniformly magnified pixels is generated representing the actual shape of the object. The true shape of the object may be displayed on an output unit, (for example, a display unit). Advantageously, the disclosure achieves determination of true shape of an object in a medical image during real-time acquisition of the medical image. For example, in a real-time fluoroscopic imaging, the true shape of the object being imaged may be determined during the interventional procedure. The obtained true shape of the object may be displayed on the display unit for further analysis by a physician. Therefore, the physician receives accurate imaging information, thereby avoiding the delay in post processing of the medical image.

Also disclosed herein is a computer program product including a non-transitory computer-readable storage medium having machine-readable instructions stored therein, that when executed by a server, cause the server to perform the method acts for obtaining a true shape of objects in a medical image.

BRIEF DESCRIPTION OF THE DRAWINGS

The present disclosure is further described hereinafter with reference to illustrated embodiments shown in the accompanying drawings, in which.

DETAILED DESCRIPTION

Hereinafter, embodiments for carrying out the present disclosure are described in detail. The various embodiments are described with reference to the drawings, wherein like reference numerals are used to refer to like elements throughout. In the following description, for purpose of explanation, numerous specific details are set forth in order to provide a thorough understanding of one or more embodiments. It may be evident that such embodiments may be practiced without these specific details.

Figure 1:
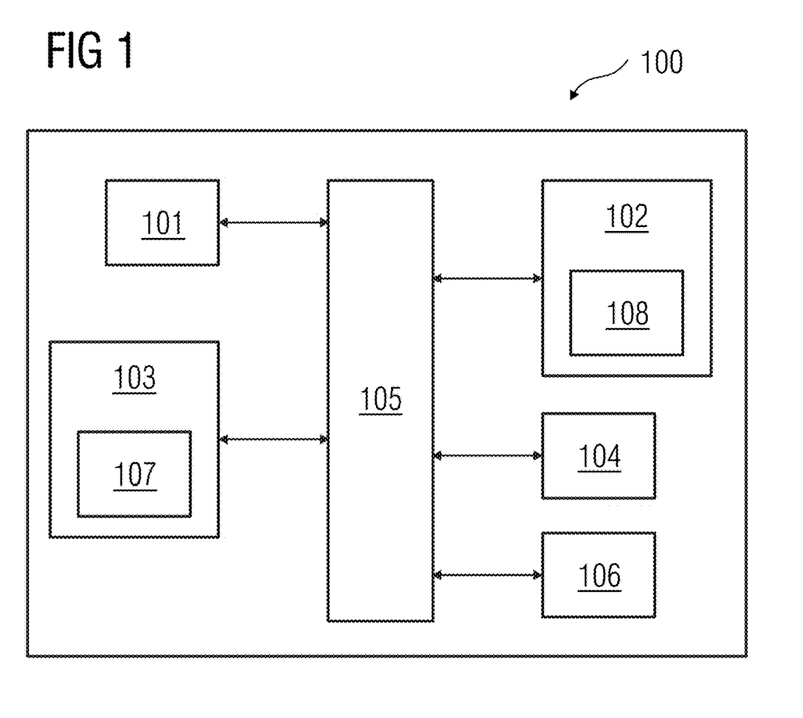
FIG. 1 illustrates a block diagram of a data processing system in which an embodiment for obtaining a true shape of an object in an X-ray image may be implemented.

FIG. 1 is a block diagram of a data processing system 100 in which an embodiment may be implemented, for example, as a system 100 for obtaining true shape of an object, configured to perform the processes as described therein. In FIG. 1, the data processing system 100 includes a processor 101, a memory 102, a storage unit 103, an input unit 104, an output unit 106 and a bus 105.

The processor 101, as used herein, refers to any type of computational circuit, such as, but not limited to, a microprocessor, microcontroller, complex instruction set computing microprocessor, reduced instruction set computing microprocessor, very long instruction word microprocessor, explicitly parallel instruction computing microprocessor, graphics processor, digital signal processor, or any other type of processing circuit. The processor 101 may also include embedded controllers, such as generic or programmable logic devices or arrays, application specific integrated circuits, single-chip computers, and the like.

The memory 102 may be volatile memory and non-volatile memory. The memory 102 may be coupled for communication with the processor 101. The processor 101 may execute instructions and/or code stored in the memory 102. A variety of computer-readable storage media may be stored in and accessed from the memory 102. The memory 102 may include any suitable elements for storing data and machine-readable instructions, such as read only memory, random access memory, erasable programmable read only memory, electrically erasable programmable read only memory, a hard drive, a removable media drive for handling compact disks, digital video disks, diskettes, magnetic tape cartridges, memory cards, and the like. In the present embodiment, the memory 102 includes a magnification correction module 108 stored in the form of machine-readable instructions on any of the above-mentioned storage media and may be in communication to and executed by processor 101. When executed by the processor 101, the magnification correction module 108 causes the processor 101 to perform correction of magnification of a plurality of pixels in an X-ray image. Method acts executed by the processor 101 to achieve the abovementioned functionality are elaborated upon in detail in FIGS. 2, 3, 4A, 4B, and 4C.

The storage unit 103 may be a non-transitory storage medium which stores an image database 107. The image database 107 is a repository of medical images related to one or more patients that is maintained by a healthcare service provider. The input unit 104 may include input devices such as a keypad, a touch-sensitive display, a camera (such as a camera receiving gesture-based inputs), etc., which are capable of receiving input signal such as a medical image. The bus 105 acts as interconnect between the processor 101, the memory 102, the storage unit 103, the input unit 104, and the output unit 106.

Those of ordinary skilled in the art will appreciate that the hardware depicted in FIG. 1 may vary for particular implementations. For example, other peripheral devices such as an optical disk drive and the like, a Local Area Network (LAN)/Wide Area Network (WAN)/Wireless (e.g., Wi-Fi) adapter, a graphics adapter, a disk controller, or an input/output (I/O) adapter also may be used in addition or in place of the hardware depicted. The depicted example is provided for the purpose of explanation only and is not meant to imply architectural limitations with respect to the present disclosure.

A data processing system 100 in accordance with an embodiment of the present disclosure includes an operating system employing a graphical user interface. The operating system permits multiple display windows to be presented in the graphical user interface simultaneously with each display window providing an interface to a different application or to a different instance of the same application. A cursor in the graphical user interface may be manipulated by a user through a pointing device. The position of the cursor may be changed and/or an event such as clicking a mouse button, generated to actuate a desired response.

One of various commercial operating systems, such as a version of Microsoft Windows™, a product of Microsoft Corporation located in Redmond, Wash., may be employed if suitably modified. The operating system is modified or created in accordance with the present disclosure as described.

Disclosed embodiments provide systems and methods for providing a true shape of objects in medical images. In particular, the systems and methods may perform magnification correction of a plurality of pixels in a medical image.

Figure 2:
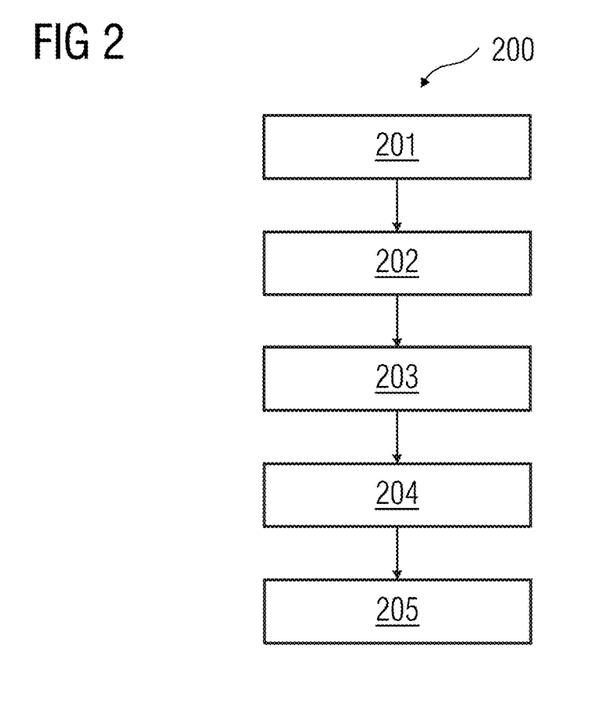
FIG. 2 illustrates a flowchart of an embodiment of a method of obtaining a true shape of an object in an X-ray image.

FIG. 2 illustrates a flowchart of an embodiment of a method 200 of obtaining a true shape of an object in a medical image. The medical image may be, for example, an X-ray image. At act 201, an X-ray image is received from the image database 107 present in the storage unit 103. The X-ray image is acquired from an imaging unit, such as an X-ray unit, and is stored in the image database 107. The X-ray image may be acquired from an X-ray unit in which X-ray source and detector are positioned at an angle. Therefore, the X-ray source and the detector are not placed perpendicular to the object plane. Therefore, the magnification across the acquired X-ray image is varied because the object plane is not perpendicular to the axis of the X-ray beam. Thus, the acquired X-ray image may not depict a true shape of the imaged object.

Figure 4A:
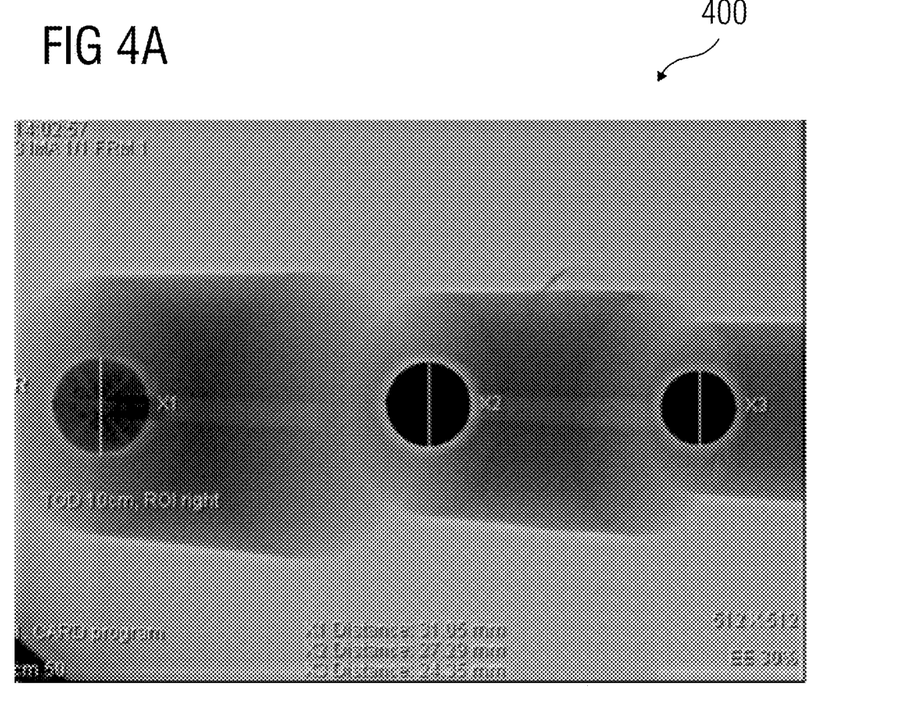
FIG. 4A illustrates an embodiment of an X-ray image in which an imaged object is deformed due to variation in magnification across the X-ray image.

FIG. 4A illustrates an embodiment of an acquired X-ray image 400 in which an imaged object is deformed due to variation in magnification across the X-ray image. The X-ray image 400 depicts three spheres, X1, X2, and X3, each sphere having an original diameter of 31.90 millimeter. However, the size of the spheres in the acquired X-ray image 400 appears different from each other. In the X-ray image 400, X1 appears bigger than X2 and X3. Furthermore, X1 appears to be deformed in comparison to X2 and X3. Due to varied magnification, the contour of X1 does not appear to be perfectly circular. FIG. 4C illustrates an embodiment of a medical imaging system 410. The medical imaging system 410 is an example of an X-ray imaging system. The X-ray imaging system 410 includes an X-ray source 401, one or more objects 402, an X-ray detector on which an image 400 of the object 402 is captured, a table 403 on which an object or patient to be imaged is placed, and a floor 406. Element 404 represents the iso-center and element 405 represents the center of the detector. Variable X depicts the height of the iso-center from the floor 406 and variable Y depicts the height of the object 402 from the table 403. The angle formed by the line joining the center of the X-ray source 401 to the center of the detector 405 with the horizontal table is depicted as Z and is known as the Angle$_{stand}$.

Figure 4B:
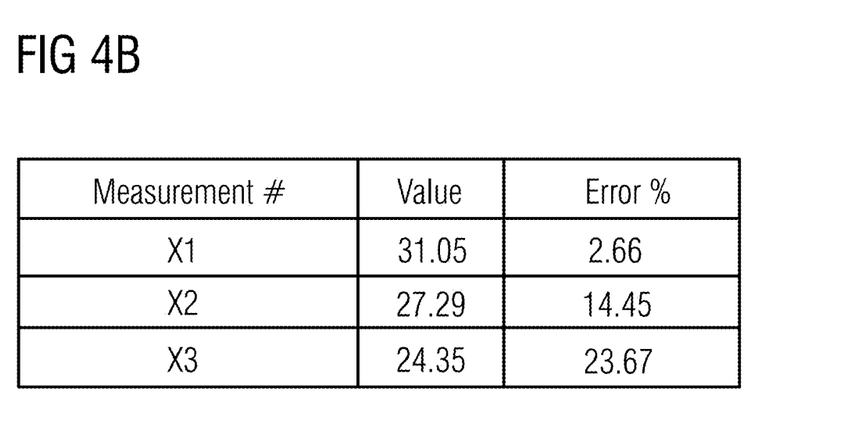
FIG. 4B illustrates a table indicating the percentage error in the values of measurement of objects in the X-ray image.
Figure 4C:
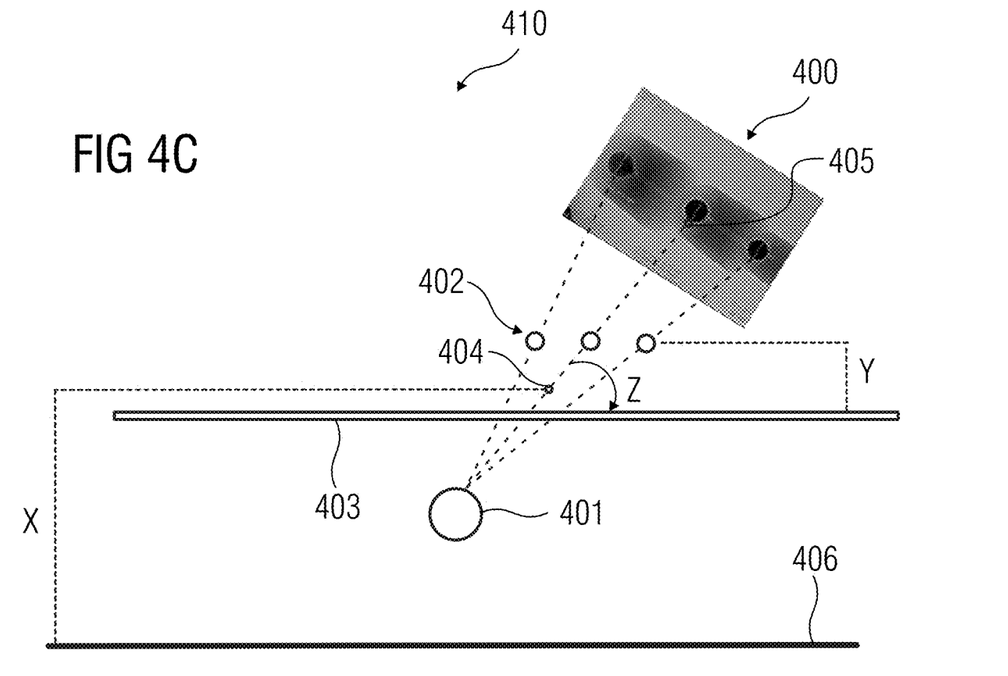
FIG. 4C illustrates an embodiment of a medical imaging system.

The percentage of error in the diameter values of X1, X2, and X3 is indicated in a table illustrated in FIG. 4B. In the table, 'Value' indicates a measured diameter value of the respective sphere in the X-ray image 400. The column 'Error %' indicates the percentage of deviation of the measured diameter value of each sphere from the actual/original diameter of the sphere.

At act 202 of the method 200, a plurality of pixels that represent an object on the X-ray image is chosen. The plurality of pixels is alternatively referred to as a contour. The plurality of pixels is chosen automatically by using any organ segmentation method that may be known to a person skilled in the art. Alternatively, the contour may be defined by a user by dragging a cursor along the desired object. Dragging the cursor along the desired object enables selection of a plurality of pixels representing the contour of the object in the X-ray image.

At act 203, magnification factor of each pixel in the X-ray image is determined. Magnification factor of a pixel in an X-ray image is determined using the below mathematical equation (1):

$$M=K/\cos(\text{Angle}_{point})/\sin(\text{Angle}_{stand}+\text{Angle}_{point}) \quad (1)$$

Where:
M: Magnification factor;
K: Stand geometry parameters which remain constant for X-ray source 401, X-ray detector, and object position 402 for a single X-ray frame;
Angle$_{point}$: An angle which a line joining X-ray source 401 to measured point (on the X-ray image) makes with a line joining X-ray source to the center of the X-ray image; and
Angle$_{stand}$: An angle Z which a line connecting the X-ray source 401 and an X-ray detector makes with a horizontal axis—the angle remains constant in a single X-ray image.

The stand geometry parameters, Angle$_{point}$, Angle$_{stand}$ are obtained from the imaging unit during the acquisition of the medical image. Alternatively, if the medical image is an image which is obtained from a database, the stand parameters and angle values may be obtained from DICOM data.

Magnification factor in an X-ray image may vary across pixels. Therefore, bringing uniformity in the magnification factor across the X-ray image enables accurate determination of size of the object in the X-ray image. At act 204 of the method 200, pixel spacing of each pixel representing the contour is determined. Pixel spacing is the physical distance between the centers of two adjacent pixels. Instead of using fixed pixel spacing, determination of pixel spacing between each set of adjacent pixels enables determination of actual size of the object in the X-ray image. Pixel spacing between adjacent pixels may be determined using the following equation (2):

$$P_{a(i,j)}=P_{o(i,j)}+M_{(i,j)} \quad (2)$$

Where:
$P_{a(i,j)}$: Actual pixel spacing between two adjacent pixels (i,j) of the X-ray image;
$P_{o(i,j)}$: X-ray detector pixel spacing between two adjacent pixels (i,j) of the X-ray image stored during X-ray acquisition; and
$M_{(i,j)}$: Magnification factor of the object calculated between two adjacent pixels (i,j) taking that point as region of interest.

Once the actual size of the object is determined, at act 250, the object is selectively reshaped to obtain a true shape of the object. The method acts involved in selectively reshaping the object in the X-ray image are explained in detail in FIG. 3.

Figure 3:
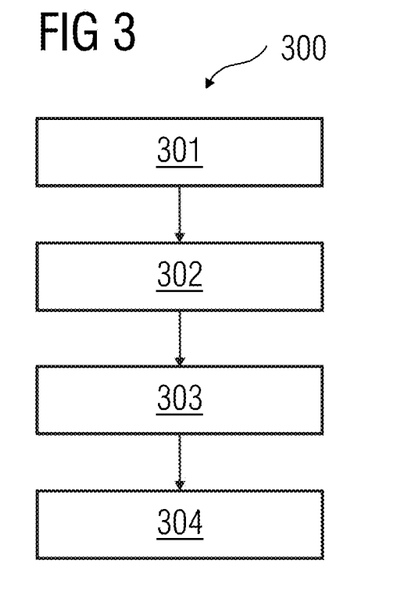
FIG. 3 illustrates a flowchart of an embodiment of a method of selectively reshaping the object in the X-ray image.

FIG. 3 illustrates a flowchart of an embodiment of a method 300 of selectively reshaping an object in an X-ray image. At act 301, a region of interest on the X-ray image, which may be deformed, is chosen for reshaping. The region of interest may be selected by the user during live acquisition of the X-ray image. The region of interest on the patient body may be chosen using X-ray stand position, beam iso-center and table-object distance Y as inputs. The region of interest may also be chosen by the user during post processing of the X-ray image. On selection of the region of interest, at act 302, a reference pixel from the region of interest is chosen such that the reference pixel is the center of the region of interest. The reference pixel may be any pixel within the region of interest. The magnification factor of the reference pixel is determined, based on which reshaping of the region of interest is performed. At act 303, the magnification of a plurality of pixels around the reference pixel is adjusted according to the magnification of the reference pixel. Therefore, the plurality of pixels around the reference pixel may be stretched or shrunk, thereby generating a sequence of uniformly magnified pixels across the X-ray image. At act 304, a rendering application renders the true shape of the object in the X-ray image using the uniformly magnified pixels. The uniformly magnified pixels enable reshaping of the deformed object in the X-ray image. Therefore, a true shape of the object in the X-ray image is achieved. In an embodiment, the true shape of the object in the X-ray image is displayed on the output unit 106. The output unit 106 may be, for example, a display unit. Advantageously, determination of true shape of an object in a medical image is achieved during real-time acquisition of the medical image. For example, in a real-time fluoroscopic imaging, the true shape of the object being imaged is determined during the interventional procedure. The obtained true shape of the object is displayed on the display unit 106 for further analysis by a physician. Therefore, the physician receives accurate imaging information, thereby avoiding the delay in post processing of the medical image. Thus, each time an image is acquired, the true shape of the object being imaged is determined and displayed to the physician in real-time. In an embodiment, the image displayed on the display unit 106 is refreshed with each acquisition.

Figure 5:
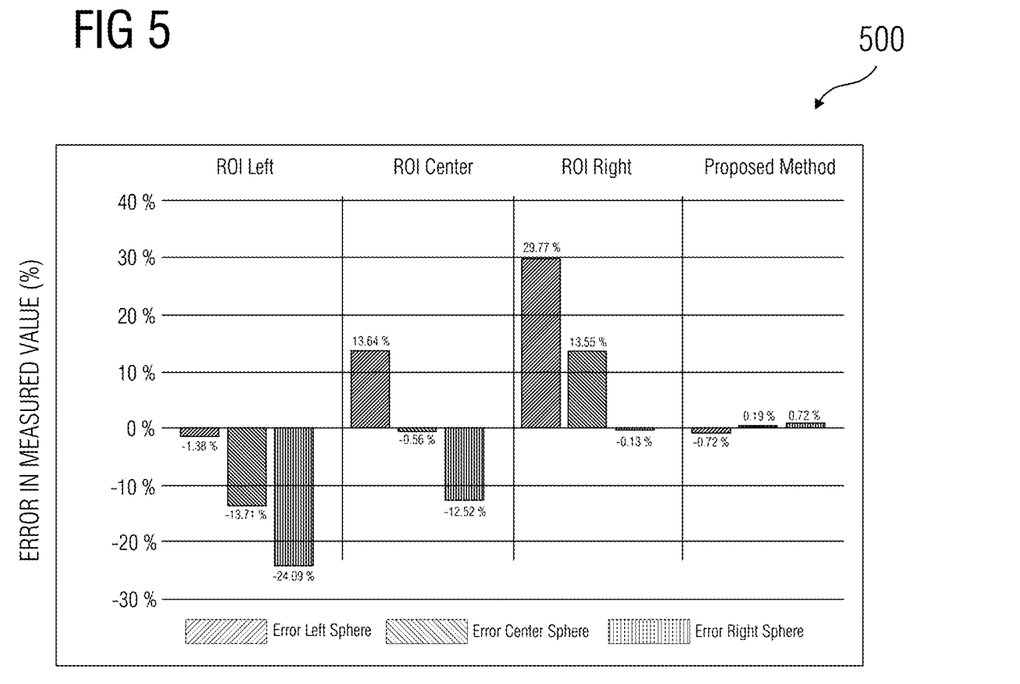
FIG. 5 illustrates an embodiment of a graph providing a comparison of object measurements performed on the X-ray image using the proposed method over techniques existing in the prior art.

FIG. 5 illustrates a graph 500 which provides a comparison of object measurements performed on the X-ray image using the proposed method over techniques existing in the prior art. In techniques existing in the prior art, a constant calibration factor is used across the X-ray image. Reference points from each sphere, X1, X2, and X3 are used for calibrating the X-ray image. When a magnification factor and pixel spacing value of a reference point from sphere X1 is used as a constant calibration factor for calibrating the X-ray image, the percentage of error in spheres X1, X2, and X3 is −1.38%, −13.71%, and −24.09% respectively. When a magnification factor and pixel spacing value of reference point from X2 is used as a constant calibration factor for calibrating the X-ray image, the percentage of error in spheres X1, X2, and X3 is 13.64%, −0.56%, and −12.52% respectively. When a magnification factor and pixel spacing value of reference point from X3 is used as a constant calibration factor for calibrating the X-ray image, the percentage of error in spheres X1, X2, and X3 is 29.77%, 13.55%, and −0.13% respectively. However, when the X-ray image is calibrated according to the proposed method, pixel spacing between each set of adjacent pixels making up the contour of the object, is determined in order to identify the actual size of the object. Furthermore, the magnification factor of the reference pixel in the region of interest is used for adjusting the magnification factor of a plurality of pixels around the reference pixel. Therefore, the plurality of pixels in the X-ray image are uniformly magnified, thereby providing an accurately calibrated X-ray image. When the proposed method is used for calibrating the X-ray image, the percentage of error in the determined true shape of the object is negligible. When a pixel from X1 is used as a reference pixel for calibrating the X-ray image, the percentage of error for X1, X2, and X3 is −0.72%, 0.19%, and 0.72%, respectively. Therefore, the proposed method enables accurate determination of actual shape of an object in an X-ray image.

The foregoing examples have been provided merely for the purpose of explanation and are in no way to be construed as limiting of the present disclosure disclosed herein. While the disclosure has been described with reference to various embodiments, it is understood that the words, which have been used herein, are words of description and illustration, rather than words of limitation. Further, although the disclosure has been described herein with reference to particular means, materials, and embodiments, the disclosure is not intended to be limited to the particulars disclosed herein; rather, the disclosure extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosure in its aspects.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method of obtaining a true shape of an object in a medical image, the method comprising:
   receiving X-ray stand geometry parameter values, an $Angle_{point}$ value, and an $Angle_{stand}$ value, wherein the $Angle_{point}$ value refers to an angle which a line joining an X-ray source to a pixel location on the medical image makes with a line joining the X-ray source to a center of the medical image, and wherein the $Angle_{stand}$ value refers to an angle which a line connecting the X-ray source and an X-ray detector makes with a line parallel to a horizontal table;
   selecting a plurality of pixels representing the object in the medical image;
   determining a magnification of each pixel in the medical image using the X-ray stand geometry parameter values, the $Angle_{point}$ value, and the $Angle_{stand}$ value;
   selecting a plurality of pixels representing a region of interest on the medical image;
   selecting a reference pixel in the region of interest; and
   reshaping the object by adjusting a magnification of the plurality of pixels of the region of interest surrounding of the reference pixel, with respect to a magnification of the reference pixel, to obtain the true shape of the object.

2. The method of claim 1, wherein, in the selecting of the plurality of pixels representing the object, the method comprises:
   identifying the plurality of pixels representing the object in the medical image; and
   selecting from the plurality of pixels a sequence of connecting pixels which represent a contour of the object.

3. The method of claim 2, further comprising:
   determining an actual size of the object by calculating pixel spacing for each pixel representing the contour of the object.

4. The method of claim 1, wherein the medical image is an X-ray image.

5. A system for obtaining a true shape of an object in a medical image, the system comprising:
   a processing unit;
   an image database coupled to the processing unit; and
   a memory coupled to the processing unit, wherein the memory and the processing unit are configured to:
      receive X-ray stand geometry parameter values, an $Angle_{point}$ value, and an $Angle_{stand}$ value, wherein the $Angle_{point}$ value refers to an angle which a line joining an X-ray source to a pixel location on a medical image makes with a line joining the X-ray source to a center of the medical image, and wherein the $Angle_{stand}$ value refers to an angle which a line connecting the X-ray source and an X-ray detector makes with a line parallel to a horizontal table;
      select a plurality of pixels representing the object in the medical image;
      determine a magnification of each pixel in the medical image using the X-ray stand geometry parameter values, the $Angle_{point}$ value, and the $Angle_{stand}$ value;
      select a plurality of pixels representing a region of interest on the medical image;
      select a reference pixel in the region of interest; and reshape the object through an adjustment of a magnification of the plurality of pixels of the region of interest surrounding of the reference pixel, with respect to a magnification of the reference pixel, to obtain the true shape of the object.

6. The system of claim 5, wherein, in the selection of the plurality of pixels representing the object, the memory and the processing unit are configured to:
identify the plurality of pixels representing the object in the medical image; and
select from the plurality of pixels a sequence of connecting pixels which represent an outline of the object.

7. The system of claim 6, wherein the memory and the processing unit are further configured to determine an actual size of the object by calculating pixel spacing for each pixel representing the outline of the object.

8. A non-transitory computer-readable storage medium having machine-readable instructions stored therein, that when executed by a server, cause the server to:
receive X-ray stand geometry parameter values, an $Angle_{point}$ value, and an $Angle_{stand}$ value, wherein the $Angle_{point}$ value refers to an angle which a line joining an X-ray source to a pixel location on a medical image makes with a line joining the X-ray source to a center of the medical image, and wherein the $Angle_{stand}$ value refers to an angle which a line connecting the X-ray source and an X-ray detector makes with a line parallel to a horizontal table;
select a plurality of pixels representing an object in the medical image;
determine a magnification of each pixel in the medical image using the X-ray stand geometry parameter values, the $Angle_{point}$ value, and the $Angle_{stand}$ value;
select a plurality of pixels representing a region of interest on the medical image;
select a reference pixel in the region of interest; and
reshape the object through an adjustment of a magnification of the plurality of pixels of the region of interest surrounding of the reference pixel, with respect to a magnification of the reference pixel, to obtain a true shape of the object.

9. The storage medium of claim 8, wherein, in the selection of the plurality of pixels representing the object, the instructions cause the server to:
identify the plurality of pixels representing the object in the medical image; and
select from the plurality of pixels a sequence of connecting pixels which represent a contour of the object.

10. The storage medium of claim 9, wherein the instructions further cause the server to:
determine an actual size of the object by calculating pixel spacing for each pixel representing the contour of the object.

11. The storage medium of claim 8, wherein the medical image is an X-ray image.

12. The storage medium of claim 8, wherein the determination of the magnification of each pixel in the medical image comprises a calculation of a magnification factor of each pixel using the following equation:

$$M=K/\cos(Angle_{point})/\sin(Angle_{stand}+Angle_{point}),$$

wherein M is the magnification factor of the respective pixel, and
wherein K is the stand geometry parameter values that remain constant for the X-ray source, the X-ray detector, and an object position for a single X-ray frame.

13. The system of claim 5, wherein the medical image is an X-ray image.

14. The system of claim 5, wherein the determination of the magnification of each pixel in the medical image comprises a calculation of a magnification factor of each pixel using the following equation:

$$M=K/\cos(Angle_{point})/\sin(Angle_{stand}+Angle_{point}),$$

wherein M is the magnification factor of the respective pixel, and
wherein K is the stand geometry parameter values that remain constant for the X-ray source, the X-ray detector, and an object position for a single X-ray frame.

15. The method of claim 1, wherein the X-ray stand geometry parameter values, the $Angle_{point}$ value, and the $Angle_{stand}$ value are obtained during acquisition of the medical image.

16. The method of claim 1, wherein the determining of the magnification of each pixel in the medical image comprises calculating a magnification factor of each pixel using the following equation:

$$M=K/\cos(Angle_{point})/\sin(Angle_{stand}+Angle_{point}),$$

wherein M is the magnification factor of the respective pixel, and
wherein K is the stand geometry parameter values that remain constant for the X-ray source, the X-ray detector, and an object position for a single X-ray frame.

* * * * *